United States Patent [19]

Zanno et al.

[11] Patent Number: 4,634,792
[45] Date of Patent: Jan. 6, 1987

[54] L-AMINODICARBOXYLIC ACID AMINOALKENOIC ACID ESTER AMIDES

[75] Inventors: Paul R. Zanno, Nanuet; Ronald E. Barnett, Suffern; Glenn M. Roy, Garnerville, all of N.Y.

[73] Assignee: General Foods Corporation, White Plains, N.Y.

[21] Appl. No.: 730,986

[22] Filed: May 6, 1985

[51] Int. Cl.$^4$ .................. C07C 101/26; C07K 5/06
[52] U.S. Cl. .................. 560/169; 260/998.21; 530/801
[58] Field of Search .......... 260/112.5 R, 998.21; 560/169; 530/801

[56] References Cited

U.S. PATENT DOCUMENTS

| | | | |
|---|---|---|---|
| 3,475,403 | 10/1969 | Mazur et al. | 260/998.21 |
| 3,492,131 | 1/1970 | Schlatter | 530/801 |
| 3,642,491 | 2/1972 | Schlatter | 260/998.21 |
| 3,695,898 | 10/1972 | Hill | 99/141 |
| 3,714,139 | 1/1973 | Schlatter | 260/998.21 |
| 3,795,746 | 3/1974 | Walton | 426/96 |
| 3,801,563 | 4/1974 | Nakajima et al. | 260/998.21 |
| 3,803,223 | 4/1974 | Mazur | 260/534 R |
| 3,907,766 | 9/1975 | Fujino et al. | 260/998.21 |
| 3,920,626 | 11/1975 | Ariyoshi et al. | 530/801 |
| 3,959,245 | 5/1976 | Nakajima et al. | 260/998.21 |
| 3,962,468 | 6/1976 | Pischke et al. | 426/96 |
| 3,971,822 | 7/1976 | Chibata et al. | 260/468 R |
| 3,978,034 | 8/1976 | Sheehan et al. | 530/801 |
| 4,011,260 | 3/1977 | Goldkamp et al. | 260/514 |
| 4,029,701 | 6/1977 | Haas et al. | 530/801 |
| 4,031,258 | 6/1977 | Haas et al. | 426/548 |
| 4,153,737 | 5/1979 | Berg et al. | 530/801 |
| 4,423,029 | 12/1983 | Rizzi | 424/54 |
| 4,439,460 | 3/1984 | Young et al. | 530/801 |
| 4,448,716 | 5/1984 | Tsau | 260/998.21 |

FOREIGN PATENT DOCUMENTS 0048051  3/1982  European Pat. Off. ....... 260/998.21

OTHER PUBLICATIONS

J. Agric. Food Chem. (1985), 33, 19-24.
Z. Lebensm. Untersuch—forsch., 159, 337-343 (1975).
Chemical Senses and Flavour 4, 141-152, (1979).
Bull. of the Chemical Society of Japan, vol. 51, (5), 1433-1440 (1978).

*Primary Examiner*—Delbert R. Phillips
*Attorney, Agent, or Firm*—Linn I. Grim; Thomas A. Marcoux; Daniel J. Donovan

[57] ABSTRACT

This invention relates to novel sweeteners of the formula:

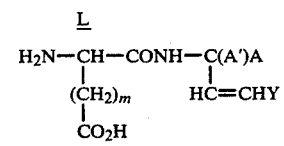

wherein
A is $CO_2R$ wherein R is alkyl containing 1-3 carbon atoms;
A' is hydrogen or alkyl containing 1-3 carbon atoms;
Y is alkyl containing 4-11 carbon atoms, and
M=0 or 1;
and food-acceptable salts thereof.

16 Claims, No Drawings

L-AMINODICARBOXYLIC ACID AMINOALKENOIC ACID ESTER AMIDES

FIELD OF THE INVENTION

This invention relates to a novel group of compounds and more particularly to a novel group of compounds particularly well suited as sweeteners in edible foodstuff.

DESCRIPTION OF THE PRIOR ART

Sweetness is one of the primary taste cravings of both animals and humans. Thus, the utilization of sweetening agents in foods in order to satisfy this sensory desire is well established.

Naturally occuring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and very objectionable bitter, metallic aftertaste when used in food products.

Since it is believed that many disadvantages of artificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose, etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener for most sweetener applications. Furthermore, the sweeteners sought must have good temporal and sensory qualities. Sweeteners with good temporal qualities produce a time-intensity sweetness response similar to natural sweeteners without lingering. Sweeteners with good sensory qualities lack undesirable off tastes and aftertaste. Furthermore, these compounds must be economical and safe to use.

In U.S. Pat. No. 3,798,204, L-aspartyl-O-t-butyl-L-serine methyl ester and L-aspartyl-O-t-amyl-L-serine methyl ester are described as sweet compounds having significant sweetness.

In U.S. Pat. No. 4,448,716 metal complex salts of dipeptide sweetners are disclosed. In the background of this patent a generic formula is described as an attempt to represent dipeptide sweeteners disclosed in five prior patents: U.S. Pat. No. 3,475,403; U.S. Pat. No. 3,492,131; Republic of South Africa Pat. No. 695,083 published July 10, 1969; Republic of South Africa Pat. No. 695,910 published Aug. 14, 1969; and German Pat. No. 2,054,554. The general formula attempting to represent these patents is as follows:

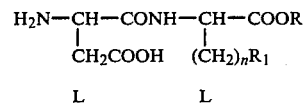

wherein R represents the lower alkyls, lower alkylaryls and cycloalkyls, n stands for integers 0 through 5, $R_1$ represents (a) phenyl group, (b) lower alkyls, (c) cycloalkyls, (d) $R_2$.

Where $R_2$ is hydroxy, lower alkoxy, lower alkyl, halogen, (e) $(S(O)_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfactory in producing a high quality sweetness or in producing a sweet response at lower levels of sweetener.

Dipeptides of aspartyl-cysteine and aspartylmethionine methyl esters are disclosed by Brussel, Peer and Van der Heijden in *Chemical Senses and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cys(t-But)-OMe
α-L-Asp-L-Met-OMe

In U.S. Pat. No. 4,399,163 to Brennan et al., sweeteners having the following formulas are disclosed:

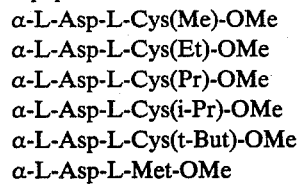

and physiologically acceptable cationic and acid addition salts thereof
wherein
$R^a$ is $CH_2OH$ or $CH_2OCH_3$;
R is a branched member selected from the group consisting of fenchyl, diisopropylcarbinyl, d-methyl-t-butylcarbinyl, d-ethyl-t-butyl-carbinyl, 2-methylthio-2,4-dimethylpentan-3-yl, di-t-butyl-carbinyl,

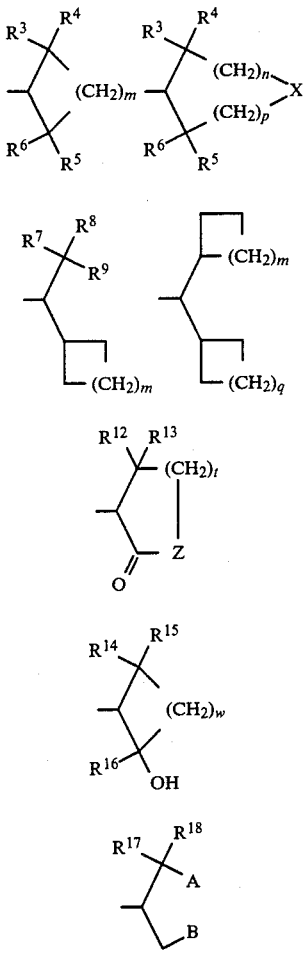

In a related patent, U.S. Pat. No. 4,411,925, Brennan, et al. disclose compounds of the above general formula with R being defined hereinabove, except $R^a$ is defined as methyl, ethyl, n-propyl or isopropyl.

U.S. Pat. No. 4,375,430 to Sklavounos discloses dipeptide sweeteners which are aromatic sulfonic acid salts of L-aspartyl-D-alaninoamides of L-aspartyl-D-serinamides.

European Patent Application No. 95772 to Tsau describe aspartyl dipeptide sweeteners of the formula:

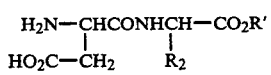

wherein $R^{40}$ is alkyl of 1 to 6 carbons, and $R_2$ is phenyl, phenylalkylenyl or cyclohexylalkenyl, wherein the alkenyl group has 1 to 5 carbons. Closely related is U.S. Pat. No. 4,439,460 to Tsau, et al. which describes dipeptide sweeteners of the formula:

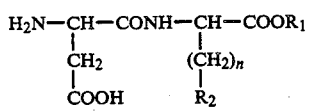

wherein n is an integer from 0 to 5, and $R_1$ is an alkyl, alkylaryl or alicyclic radical. Similar such compounds are described in many related patents, the major difference being the definition of $R_2$.

In U.S. Pat. No. 3,978,034 to Sheehan, et al., $R_2$ is defined as cycloalkenyl or phenyl. U.S. Pat. No. 3,695,898 to Hill defines $R_2$ as a mono- or a di-unsaturated alicyclic radical. Haas, et al. in U.S. Pat. No. 4,029,701 define $R_2$ as phenyl, lower alkyl or substituted or unsubstituted cycloalkyl, cycloalkenyl or cycloalkdienyl, or $S(O)_m$ lower alkyl provided that n is 1 or 2 and m is 0 or 2. Closely related are U.S. Pat. Nos. 4,448,716, 4,153,737 4,031,258, 3,962,468, 3,714,139, 3,642,491, and 3,795,746.

U.S. Pat. No. 3,803,223 to Mazur, et al. describe dipeptide sweeteners and anti-inflammatory agents having the formula:

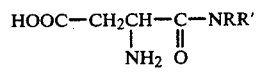

wherein R is hydrogen or a methyl radical and R' is a radical selected from the group consisting of alkyl, or

wherein Alk is a lower alkylene radical, X is hydrogen or hydroxy, and Y is a radical selected from the group consisting of cyclohexyl, naphthyl, furyl, pyridyl, indolyl, phenyl and phenoxy.

Goldkamp, et al. in U.S. Pat. No. 4,011,260 describe sweeteners of the formula:

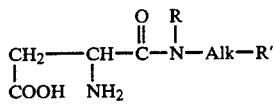

wherein R is hydrogen or a lower alkyl radical, Alk is a lower alkylene radical and R' is a carbocyclic radical. Closely related is U.S. Pat. No. 3,442,431.

U.S. Pat. No. 4,423,029 to Rizzi describes sweeteners of the formula:

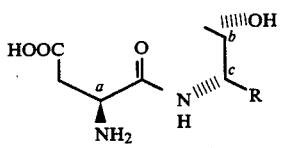

wherein R is $C_4$–$C_9$ straight, branched of cyclic alkyl, and wherein carbons a, b and c have the (S) configuration.

European Patent Application No. 48,051 describes dipeptide sweeteners of the formula:

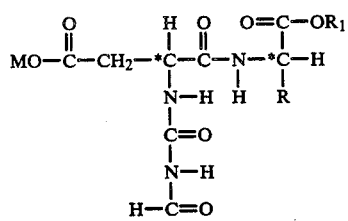

wherein

M represents hydrogen, ammonium, alkali or alkaline earth,

R represents

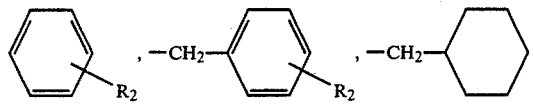

$R_1$ represents methyl, ethyl, propyl,
$R_2$ represents —OH, or $OCH_3$,
\* signifies an L-optical configuration for this atom.

German Patent Application No. 7259426 discloses L-aspartyl-3-fenchylalanine methyl ester as a sweetening agent.

U.S. Pat. No. 3,971,822 to Chibata, et al., disclose sweeteners having the formula:

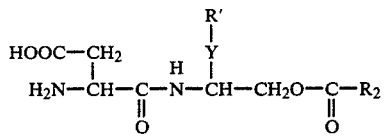

wherein R' is hydrogen or hydroxy, $R_2$ is alkyl of one to five carbon atoms, alkenyl of two to three carbon atoms, cycloalkyl of three to five carbon atoms or methyl cycloalkyl of four to six carbon atoms and Y is alkylene of one to four carbon atoms.

U.S. Pat. No. 3,907,366 to Fujino, et al. discloses L-aspartyl-aminomalonic acid alkyl fenchyl diester and its' physiologically acceptable salts as useful sweeteners. U.S. Pat. No. 3,959,245 disclose the 2-methyl cyclohexyl analog of the abovementioned patent.

U.S. Pat. No. 3,920,626 discloses N-αL-aspartyl derivatives of lower alkyl esters of O-lower-alkanoyl-L-serine, β-alanine, γ-aminobutyric acid and D-β-aminobutyric acid as sweeteners.

Miyoshi, et al. in *Bulletin of Chemical Society of Japan*, 51, p. 1433–1440 (1978) disclose compounds of the following formula as sweeteners:

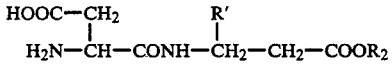

wherein R' is H, $CH_3$, $CO_2CH_3$, or benzyl and $R_2$ is lower alkyl or unsubstituted or substituted cycloalkyl.

European Patent Application No. 128,654 describes gem-diaminoalkane sweeteners of the formula:

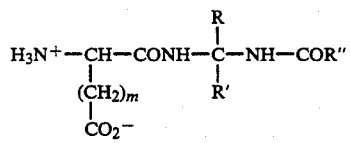

wherein m is 0 or 1, R is lower alkyl (substituted or unsubstituted), R' is H or lower alkyl, and R" is a branched alkyl, alkylcycloalkyl, cycloalkyl, polycycloalkyl, phenyl, or alkyl-substituted phenyl, and physically acceptable salts thereof.

U.S. Pat. No. 3,801,563 to Nakajima, et al. disclose sweeteners of the formula:

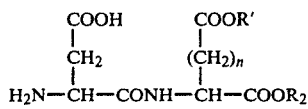

wherein R' is a branched or cyclic alkyl group of 3 to 8 carbon atoms, $R_2$ is a lower alkyl group of 1 to 2 carbon atoms and n is a integer of 0 or 1.

Rizzi, in J. Agric., Food Chem. 33, 19–24 (1985) synthesized sweeteners of the Formulas:

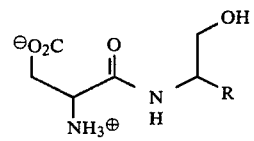

wherein

R = lower alkyl
i-$C_3H_7$—CH=CH—
i-$C_3H_7$—CH=CH—
$(CH_3)_2C$=CH—$CH_2$—
and wherein $R^1$ = H, $CH_3$
R = lower alkyl
i-$C_3H_7$—CH=CH—

European Patent Application No. 34,876 describes amides of L-aspartyl-D-amino acid dipeptides of the formula:

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of significant sweetness.

In the *Journal of Medicinal Chemistry*, 1984, Vol. 27, No. 12, pp. 1663–8, are described various sweetener dipeptide esters, including L-aspartyl-α-aminocycloalkane methyl esters.

The various dipeptide esters of the prior art have been characterized as lacking significant stability at low pH values and/or thermal stability. These characteristics have limited the scope of use of these sweeteners in food products which are of low pH values or are prepared or served at elevated temperatures.

Accordingly, it is desired to find compounds that provide quality sweetness when added to foodstuffs or pharmaceuticals at low levels and thus eliminate or greatly diminish the aforesaid disadvantages associated with prior art sweeteners.

SUMMARY OF THE INVENTION

The present new compounds are esters of certain α-aminodicarboxylic acids and α-aminoesters which are low calorie sweeteners that possess a high order of sweetness with pleasing taste and higher stability at acid pH and elevated temperatures compared to known dipeptide sweeteners.

This invention provides new sweetening compounds represented by the formula:

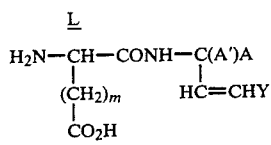

wherein
A is $CO_2R$ in which R is alkyl containing 1–3 carbon atoms;
A' is hydrogen or alkyl containing 1–3 carbon atoms;
Y is alkyl containing from 4 to 11 carbon atoms; and
m=0 or 1;
and food-acceptable salts thereof.

DESCRIPTION OF PREFERRED EMBODIMENTS

The alkyl groups representative of the substituent Y are normal or branched chain alkyl groups including, for example, isobutyl, t-butyl, t-amyl, isooctyl, isobutylmethyl, t-butylmethyl, isoamyl, t-amyl, di-t-butylmethyl, sec-pentyl, sec-hexyl, 3-pentyl, 3-hexyl, 3-heptyl, 3-octyl, 4-heptyl, 4-octyl, 4-nonyl, 5-nonyl, methylisopropylmethyl, methyl-t-butylmethyl, methyl-t-amylmethyl, ethylisopropylmethyl, ethyl-t-amylmethyl, isopropyl-t-butylmethyl, t-butyl-t-amylmethyl, diisopropylmethyl, di-t-amylmethyl, ethyl-t-butylmethyl, and similar alkyl groups. Particularly preferred alkyls diisopropylmethyl, di-t-amylmethyl, ethyl-t-butylmethyl, and similar alkyl groups. Particularly preferred alkyls are of the formula $-CH(R_1)(R_2)$ wherein $R_1$ is H or lower alkyl and $R_2$ is alkyl, provided that $-CH(R_1)(R_2)$ contains at least 6 carbon atoms. Of these, the preferred are branched chain alkyls, particularly tertiary alkyls. The most preferred are $-CH(R_1)(R_2)$ alkyls in which each of $R_1$ and $R_2$ is tertiary alkyl, e.g. t-butyl or secondary alkyl, e.g. isopropyl.

These novel compounds are effective sweetness agents when used alone or in combination with other sweeteners in an ingesta, e.g., foodstuffs or pharmaceuticals. For example, other natural and/or artificial sweeteners which may be used with the novel compounds of the present invention include sucrose, fructose, corn syrup solids, dextrose, xylitol, sorbitol, mannitol, acetosulfam, thaumatin, invert sugar, saccharin, thiophene saccharin, meta-aminobenzoic acid, metahydroxybenzoic acid, cyclamate, chlorosucrose, dihydrochalcone, hydrogenated glucose syrups, aspartame (L-aspartyl-L-phenylalanine methyl ester) and other dipeptides, glycyrrhizin and stevioside and the like. These sweeteners when employed with the sweetness agents of the present invention, it is believed, could produce synergistic sweetness responses.

Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds are experienced over a wide pH range, e.g. 2 to 10 preferably 3 to 7 and in buffered and unbuffered formulations.

It is desired that when the sweetness agents of this invention are employed alone or in combination with another sweetner, the sweetener or combination of sweeteners provide a sucrose equivalent in the range of from about 2 weight percent to about 40 weight percent and more preferably from about 3 weight percent to about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention, several reaction schemes may be employed. In one reaction scheme, compounds of general formula II (a protected α-aminodicarboxylic acid) and III (3-amino-1-propene derivatives) are condensed to form compounds of general formula I:

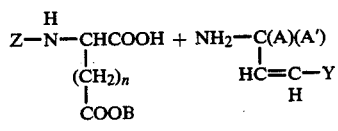

II            III

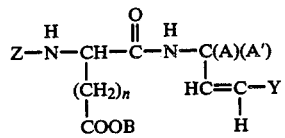

IV

In these, Z is an amino protecting group, B is a carboxy protecting group, and A, A', Y, and n have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for A and benzyl for B.

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethyl-aminopyridine or copper (II). The DCC coupling reaction generally proceeds at room temperature, however, it may be carried out from about $-20°$ to $50°$ C. in a variety of solvents inert to the reactants. Thus suitable solvents include, but are not limited to, N,N-dimethyl-formamide, methylene chloride, toluene and the like. Preferably the reaction is carried out under an inert atmosphere such as argon or nitrogen. Coupling usually is complete within 2 hours but may take as long as 24 hours depending on reactants.

Various other amide-forming methods can be employed to prepare the desired compounds using suitable derivatives of the free-carboxy group in compounds of structure II, e.g., acid halide, mixed anhydride with acetic acid and similar derivatives. The following illustrates such methods using aspartic acid as the amino dicarboxylic acid.

One such method utilizes the reaction of N-protected aspartic anhydrides with the selected amino compound of formula III. Thus compounds of formula III can be reacted directly in inert organic solvents with L-aspartic anhydride having its amino group protected by a formyl, carbobenzloxy, or p-methoxycarbobenzloxy group which is subsequently removed after coupling to give compounds of general formula I. The N-acyl-L-aspartic anhydrides are prepared by reacting the corresponding acids with acetic anhydride in amounts of 1.0-1.2 moles per mole of the N-acyl-L-aspartic acid at $0°$ to $60°$ C. in an inert solvent. The N-acyl-L-aspartic anhydrides are reacted with preferably 1 to 2 moles of compounds of formula III in an organic solvent capable of dissolving both and inert to the same. Representative solvents are ethyl acetate, methyl propionate, tetrahydrofuran, dioxane, ethyl ether, N,N-dimethylformamide and benzene. The reaction proceeds smoothly at $0°$ to $30°$ C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of $-10°$ to $50°$ C. and at a pH of 4-12.

Compounds of general formula III are synthesized using art recognized techniques. For example, compounds of formula III can be synthesized by the dehydration of the corresponding alcohol, which is formed by reacting a Grignard reagent of formula V with an aldehyde (VI)

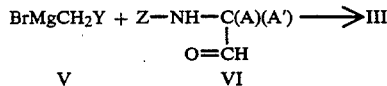

V  VI

The Grignard reaction generally proceeds at $0°$ C., however, it may be carried out from about $-200°$ C. to $50°$ C. in a variety of solvents inert to the reactants. Thus, suitable solvents include diethylether, tetrahydrofuran, and the like.

Alternatively, compound VI is reacted with the appropriate Wittig reagent under art-recognized conditions, e.g.,

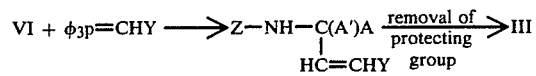

Compounds of formula V are prepared by art recognized procedures from commerically available starting materials. One such method involves reacting the appropriate Wittig reagent, such as methoxymethyltriphenylphosphonium chloride with ketone, such as cyclopentanone, in the presence of a strong base, e.g., sec-butyllithium, to form the corresponding enol-ether, which is hydrolyzed and then reduced by typical reducing agents, such as sodium borohydride to form a halide from which the Grignard reagent is prepared.

The aldehyde (VI) is itself prepared from reduction of an amino acid or its corresponding ester. Typical reducing agents include (iso-Bu)$_2$AlH, LiAlH$_4$ and Bis(N-methylpiperazinyl) aluminum hydride. Typical temperatures for this reaction are in the range of $-70°$ to room temperature. The reaction is carried out in solvents which are inert to both reactants and products and will dissolve both reactants. Examples include tetrahydrofuran, diethylether, methylene chloride, dimethyl formamide and the like.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from $5°$ to $65°$ C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

It is known to those skilled in the art that the compounds of the present invention having asymmetric carbon atoms may exist in racemic or optically active forms. All of these forms are contemplated within the scope of the invention.

The compounds of the present invention have one asymmetric site, which is designated by an asterik (*) in the formula below, and one pseudoasymmetric site which is designated by a double asterik (**):

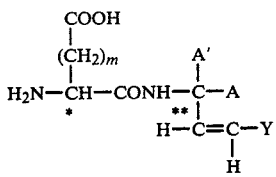

Whenever A is identical to A', the compounds of the present invention have only one asymmetric site, designated by the asterik, in the dicarboxylic acid moiety.

Although both the D and L forms are possible; the preferred compounds are those in which the dicarboxylic acid group is in the L-configuration. Whenever, the groups A' and A are different, the carbon atoms designated by the double asteriks become assymmetric centers and the compounds of the present invention will contain at least two asymmetric centers. Regardless, the configuration around each of the asymmetric sites, whenever present, may exist in either the D or L forms, and all possible stereoisomers are contemplated to be within the scope of the present invention.

The presence of the double bond in the vinyl substituent also creates, geometric isomers, which can exist in either the cis- or trans-forms. The trans stereoisomer is the preferred species. Thus, the compounds of the present invention are diastereomers, which can be separated, if desired, by art-recognized techniques, as, for example, chromatography. However, mixtures of at least any two stereoisomers exhibit sweetness properties and are useful as sweeteners.

The following examples further illustrate the invention.

EXAMPLE 1

N-L-Aspartyl-2-amino-4-(di-t-butylmethyl)but-3-enoic acid methyl ester

A solution of t-butyl bromide in ether is added slowly to magnesium stirrings until the Grignard reagent begins to form. The remainder of the alkyl bromide is then added and the mixture is stirred until all the magnesium dissolves. At 0° C., a solution of 2,2-dimethylpropionaldehyde is added and the resulting product is quenched with 1M HCl and extracted with ether and the solvent is evaporated to afford di-t-butylmethyl alcohol.

The alcohol is dissolved in benzene and stirred at 0° C. under argon. A solution of phosphorus tribromide in benzene is added and the mixture is stirred for 2 hours and then heated to 60° C. for 4 hours. The mixture is cooled, poured into ice and extracted with ether. The organic layer is washed with saturated NaHCO$_3$, dried over MgSO$_4$ and evaporated to give di-t-butylmethyl bromide.

Dibenzyl malonate (10.0 g, 35.2 mmol) is taken up in 1,4-dioxane (100 mL) and treated with a 40% aqueous solution of acetic acid (35 mL), followed by the slow addition (2.5 h) of solid sodium nitrite (10 g). The reaction is stirred for another 2.5 hours and extracted into ether (3×70 mL). The organic phase is washed with a 1% solution of NaHCO$_3$ until the aqueous layer is slightly acidic (pH 5-6). The ethereal solution is dried over MgSO$_4$ and removed under reduced pressure to give an oil (10.9 g). The crude oxime is carried directly to the next step.

Amalgamated aluminum (obtained from 1.25 g, 0.463 g atom of aluminum foil) is covered with tetrahydrofuran (28 mL), followed by 1.9 mL of water. The reaction mixture is stirred mechanically and cooled in a dry ice acetone bath. A solution of the crude oxime (from the previous step) in 30 mL of tetrahydrofuran is added dropwise (20 min.) while the temperature is maintained between −15° and −30° C. The ice bath is removed and a spontaneous reaction occured, which results in a rapid rise in temperature (50° C.). When the evolution of heat ceases, the mixture is refluxed for 1 hour, diluted with ether (100 mL), and filtered through Celite. The solvent is removed under reduced pressure to give the crude amine (7.5 g), which is taken to the following step without further purification.

A small sample (0.5 g) of the crude amine is taken up in dry ether (10 mL) and treated with HCl gas at 0° C. The amine hydrochloride is collected by filtration, washed with ether, dried in vacuo, and recrystallized from MeOH/i-Pr$_2$O.

The crude amine (7 g) is dissolved in a saturated solution of NaHCO$_3$ (200 mL) and cooled in an ice bath. Benzyl chloroformate (4.0 g, 23 mmol) is added dropwise (0.5 h) to the vigorously stirred solution. The reaction mixture is left at room temperature for 12 hours, during which time the product precipitates. The product is collected by filtration, washed with water, dried in air, and recrystallized from i-PrOH: yield 4.8 g (52%), from dibenzyl malonate.

The above product is dissolved in acetone/water (4:1, 133 mL). The solution is stirred and lithium hydroxide monohydrate (0.42 g, 10 mmol) in water (11 mL) is added dropwise (1 h). The reaction mixture is stirred for 12 hours at room temperature, the acetone is removed under reduced pressure, and the residue is taken up into a saturated solution of NaHCO$_3$ (60 mL) and extracted with EtOAc (3×100 mL). The EtOAc washings are combined, dried over MgSO$_4$, and removed under reduced pressure to give a solid, which is crystallized from EtOAc/hexane. This solid is identified as recovered starting material (1.1 g, 25.4%). The aqueous phase is acidified with 3N HCl to pH≃1 and extracted with CHCl$_3$ (4×50 mL). The combined CHCl$_3$ washings are dried over MgSO$_4$, and the solvent is removed under reduced pressure to give a residue which is crystallized from i-PrOH to afford N-Cbz-aminomalonic acid mono-benzyl ester.

The above product is dissolved in tetrahydrofuran and stirred at 0° C. under argon. Bis(N-methylpiperazinyl)aluminum hydride is added and the reaction mixture is heated to reflux overnight. Ether is then added and the excess hydride is quenched with saturated NaCl. The combined organic phases are washed with 2M NaOH$_3$ in 2M HCl and saturated NaCl. The solution is dried over Na$_2$SO$_4$ and evaporated to yield the 2-benzyloxycarbonyl-2-CBZ-aminoacetaldehyde.

Triphenylphosphine is suspended in toluene. Di-t-butylmethyl bromide is added and the reaction is refluxed overnight. The mixture is cooled and the phosphonium salt is collected by vacuum filtration.

The di-t-butylmethyl triphenylphosphonium bromide is suspended in tetrahydrofuran at 0° C. under argon. Sec-Butyl-lithium in cyclohexane is added followed by a solution of 2-benzyloxycarbonyl-2-CBZ-aminoacetaldehyde in tetrahydrofuran. After one hour, water is added to the reaction mixture. The organic layer is separated, washed with water and dried over MgSO$_4$ and evaporated to yield the alkene, benzyl 2-CBZ-amino-4-(di-t-butylmethyl)-3-butenoate.

The above product is dissolved in absolute alcohol at 0° C. in an ultrasound bath. Palladium on carbon is added. The hydrogen source, 1,4-cyclohexadiene is added and ultrasound is commenced for eight minutes. The slurry is then filtered through a bed of Celite with ethyl alcohol. The solvent is removed to afford 2-amino-4-(di-t-butylmethyl)but-3-enoic acid.

The above product is dissolved in ether and is reacted with diazomethane (which is generated in situ from N-Nitrosomethyl urea and potassium hydroxide) at 5° C. and under N$_2$. The ether is evaporated to afford the methyl 2-amino-4-(di-t-butylmethyl)-3-butenoate.

To a magnetically stirred solution of the above product in dry dimethylformamide at 0° C. under argon is added N-Cbz-L-aspartic acid beta-benzyl ester followed by copper (II) chloride and dicyclohexylcarbodiimide. This is stirred for 18 hours, after which the reaction mixture is poured into 0.1N HCl and extracted with ethyl acetate. The organic phase is washed with saturated NaHCO$_3$ and then water, and dried over MgSO$_4$. The solvent is evaporated.

The above product is dissolved in absolute alcohol at 0° C. in an ultrasound bath. Palladium on carbon (10%) is added. The hydrogen source, 1,4-cyclohexadiene, is added, and ultrasound is commenced for eight minutes. The slurry is then filtered through a bed of Celite with ethyl alcohol. The solvent is removed by rotary evaporation to afford the final product and the corresponding butanoic acid methyl derivatives, which are separated by column chromatography on silica gel.

Similarly, by using the appropriate starting materials, the following additional compounds are prepared:

N-L-aspartyl-2-amino-4-(2,2,5-trimethylcyclopentyl)-but-3-enoic acid methyl ester.

N-L-aspartyl-2-amino-4-(2,5-dimethylcyclopentyl)but-3-enoic acid methyl ester.

N-L-aspartyl-2-amino-4-(dicyclopropylmethyl)but-3-enoic acid methyl ester.

N-L-aspartyl-2-amino-4-(fenchyl)but-3-enoic acid methyl ester.

N-L-aspartyl-2-amino-4-(2-t-butylcyclopentyl)but-3-enoic acid methyl ester.

N-L-aspartyl-2-amino-4-(1-t-butyl-1-cyclopropylmethyl)but-3-enoic acid methyl ester.

N-L-aspartyl-2-amino-4-(1-isopropyl-1cyclopropylmethyl)but-3-enoic acid methyl ester.

The compounds of the present invention possess higher sweetness and/or stability in comparison with comparable compounds of the prior art.

For example, in present experience, the present new compounds are substantially sweeter than aspartame, the present commercially-used synthetic dipeptide sweetener, especially those in which Y=CHR$_1$R$_2$ where R$_1$ and R$_2$ are branched-chain alkyls, particularly tertiary alkyls. The present compounds are significantly sweeter than corresponding compounds in which Y is lower alkyl, e.g., methyl or isopropyl.

What is claimed is:

1. A compound represented by the formula:

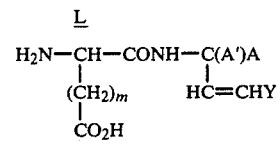

wherein
A is CO$_2$R wherein R is alkyl containing 1-3 carbon atoms;
A' is hydrogen or alkyl containing 1-3 carbon atoms;
Y is alkyl containing 4-11 carbon atoms, and
M=0 or 1;
and food-acceptable salts thereof.

2. A compound according to claim 1 wherein Y is —CHR$_1$R$_2$ containing at least 6 carbon atoms in which R$_1$ is H or lower alkyl and R$_2$ is lower alkyl.

3. A compound according to claim 2 wherein at least one of R$_1$ and R$_2$ is a branched chain alkyl.

4. A compound according to claim 2 wherein at least one of R$_1$ and R$_2$ is a tertiary alkyl.

5. A compound according to claim 2 wherein R$_1$ and R$_2$ are tertiary alkyls.

6. A compound according to claim 5 wherein the tertiary alkyl is t-butyl.

7. A trans-alkene compound represented by the formula:

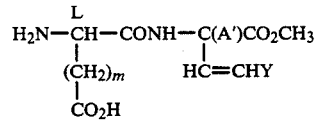

wherein:
A' is H or alkyl containing 1-3 carbon atoms;
Y is alkyl containing 4-11 carbon atoms; and
m=0 or 1;
and food-accepted salts thereof.

8. A compound according to claim 1 wherein Y is —CHR$_1$R$_2$ containing at least 6 carbon atoms in which R$_1$ is H or lower alkyl and R$_2$ is lower alkyl.

9. A compound according to claim 8 wherein at least one of R$_1$ and R$_2$ is a branched chain alkyl.

10. A compound according to claim 9 wherein at least one of R$_1$ and R$_2$ is a tertiary alkyl.

11. A compound according to claim 9 wherein R$_1$ and R$_2$ are tertiary alkyls.

12. A compound according to claim 11 wherein the tertiary alkyl is t-butyl.

13. The compound according to claim 7 which is N-L-aspartyl 2-amino-4-(di-t-butylmethyl)but-3-enoic acid methyl ester.

14. The compound according to claim 7 which is N-L-aspartyl 2-amino-4-(d-t-amylmethyl)but-3-enoic acid methyl ester.

15. The compound according to claim 7 which is N-L-aspartyl 2-amino-4-(diisopropylmethyl)but-3-enoic acid methyl ester.

16. The compound according to claim 7 which is N-L-aspartyl 2-amino-4-t-butylmethylbut-2-enoic acid methyl ester.

* * * * *